United States Patent [19]
Kane

[11] Patent Number: 4,903,534
[45] Date of Patent: Feb. 27, 1990

[54] METHOD AND APPARATUS FOR TESTING BRUSHES

[75] Inventor: Patricia L. Kane, Hauppauge, N.Y.
[73] Assignee: Estee Lauder, Inc., New York, N.Y.
[21] Appl. No.: 280,830
[22] Filed: Dec. 7, 1988
[51] Int. Cl.$^4$ ............................................. G01N 19/00
[52] U.S. Cl. .................................................. 73/865.9
[58] Field of Search ....................... 73/7, 865.9, 150 R, 73/150 A; 15/1, 21 B, 21 C, 21 D, 21 E, 22 A, 33, 256.53, 256.5; D4/124, 125, 137

[56] References Cited
U.S. PATENT DOCUMENTS

| 2,498,265 | 2/1950 | Green ........................................ 73/7 |
| 3,100,981 | 8/1963 | Engle et al. ............................... 73/7 |
| 3,974,678 | 8/1976 | Rooney et al. ...................... 73/150 R |
| 4,042,997 | 8/1977 | McDowell et al. ................... 15/366 |
| 4,134,935 | 1/1979 | Quiring et al. ....................... 525/440 |

OTHER PUBLICATIONS
Gardner, "Gardner Electrically Operated Straight-Line Washability Machine", Gardner Laboratory, Inc., Bethesda, Md., May 1947.
Gardner, "Washability Machine", Gardner Laboratory, Inc., Bethesda, Md., May 1941.

Primary Examiner—Robert R. Raevis
Attorney, Agent, or Firm—Robert M. Isackson

[57] ABSTRACT

A method and apparatus of testing brushes for: (a) determining the dye transfer characteristics of brushes having dyed bristles, and (b) determining the capacity of brushes for picking-up acceptable amounts of product and transferring the product to an application surface. The method and apparatus of the invention are particularly useful for testing cosmetic brushes.

8 Claims, 3 Drawing Sheets

METHOD AND APPARATUS FOR TESTING BRUSHES

This invention relates to a method and apparatus for testing brushes, particularly cosmetic brushes, for acceptable levels of dye transfer from the bristles of the brush and/or acceptable pick-up of particulate products by the bristles of the brush and transfer of those products to an application surface.

BACKGROUND OF THE INVENTION

Brushes are typically composed of a rigid shaft and bristles that are attached to the shaft. The bristles may be made of either natural animal hair, e.g., goat, pony, badger, etc., or synthetic hair, e.g., nylon fibers. The color of natural animal hair bristles is not uniform and may vary both within a brush and from brush to brush. Synthetic bristles may be colorless, or may be produced being colored throughout, with the color frequently differing from batch to batch.

For various marketing and aesthetic reasons, it is frequently desirable to provide the bristles of a given brush with a uniform color. This is particularly so in the cosmetic industry where aesthetic considerations are very important and it is frequently desirable to utilize brush bristles that match or complement in a visually pleasing fashion the color of a given cosmetic product. It also is desirable for marketing reasons to provide brush bristles with a uniform color from brush to brush. Consequently, it has become common for brush manufacturers, particularly manufacturers of brushes for cosmetic use, to dye brush bristles to the desired uniform color.

One of the problems with dyed brush bristles is that excessive dye is often applied to the bristles, which rubs off the bristles onto the product or the application area (or both) when the brush is used. Another problem is that the dyes used do not always adhere to the bristles well, even when applied to the bristles in moderate amount, and consequently rub off during use. Although some dye transfer is acceptable, it is desirable to minimize such dye transfer to avoid dye being visible on the application area or in apparent discoloration of the product being applied.

Heretofore, brushes have been subjectively evaluated for dye transfer by having an inspector use the brush. Such testing is subject to operator variation, particularly inconsistent pressure on the bristles while testing from brush to brush or even while testing the same brush. Such subjective tests are difficult to apply consistently in order to obtain consistently high quality products.

Similarly, it has been difficult to evaluate the relative ability of different brushes to pick-up product for delivery of the product to the application area. It is also difficult to evaluate the relative ability of different brushes to transfer product to an application surface (e.g., the skin) in use. Subjective evaluations for such pick-up capacity and subsequent transfer capacity are difficult to apply consistently in order to ensure that brushes appropriate for a particular product and application are consistently provided.

It is, therefore, an object of this invention to provide a method of testing dyed brushes in a consistent and repeatable fashion to determine whether or not the brushes exhibit excessive dye transfer characteristics. It is another object of the invention to provide a method that permits comparative testing of different dyed brushes to determine their relative dye transfer characteristics. It is another object to provide an apparatus for conducting such testing.

It is also an object of this invention to provide a method of testing brushes in a consistent and repeatable fashion to determine how much product a particular type of brush will pick-up from a source and ultimately transfer to the application area. It is another object to provide an apparatus for conducting such testing.

SUMMARY OF THE INVENTION

One preferred embodiment of this invention is directed to a method of testing brushes having dyed bristles to determine whether or not in use an excessive amount of dye would be transferred either into the product for which the brush is being used (e.g., a cosmetic) or onto an application surface (e.g., a person's skin). That method comprises the following steps:

(a) providing a test sample application area;
(b) providing a device for holding the brush at a predetermined position with respect to the test sample application area; the predetermined position being selected so that the dyed bristles of the brush may be moved in relative contact with the test sample application area;
(c) placing the brush in the device and moving the bristles of the brush in relative contact with the test sample application area over a predetermined distance a predetermined number of times; and
(d) examining the test sample application area to determine whether or not the amount of dye transferred to that area is acceptable.

In preferred embodiments for testing brushes having dyed bristles, the test sample application area comprises white paper, most preferably 100% bond grade white paper. In use, the white paper is temporarily secured (e.g., by a pair of spaced clamps) to the remainder of the test sample application area. During step (c) above, dye may be transferred from the dyed brush bristles to the white paper. The extent of such transfer and whether or not the brush is acceptable can be readily judged by comparing the color of the dye on the white sheet to a standard that was heretofore prepared.

In another preferred embodiment of the invention, a method is provided for testing the capacity of a brush to pick-up an acceptable amount of a product (e.g., a cosmetic product). That method comprises the following steps:

(a) providing a sample of product at a fixed position at a test sample application area;
(b) providing a device for holding a brush at a predetermined position with respect to sample of product, the predetermined position being selected so that the bristles of the brush may be moved in relative contact with the sample of product;
(c) placing the brush in the device and moving the bristles of the brush in relative contact with the sample of product a predetermined distance a predetermined number of times; and
(d) determining whether or not the amount of product pick-up by the brush in step (c) above is acceptable.

A preferred method for making the determination in step (d) above comprises weighing the brush both before and after step (c) is conducted. A similar method comprises weighing the sample of product before and after step (c) is conducted. Obviously, the amount of product transferred in each of these embodiments can be determined by simple subtraction.

Another method for determining the adequacy of the pick-up involves determining the adequacy of subsequent transfer of the product from the brush. That method comprises the further steps:

(e) removing the sample of product from the test sample application area;

(f) after conducting step (d), replacing the brush in the device a predetermined distance from the test sample application area, the predetermined position being selected so that the bristles of the brush may be moved in relative contact with the test sample application area;

(g) moving the bristles of the brush in relative contact with the test sample application area a predetermined distance a predetermined number of times; and (h) determining whether or not the amount of product transferred from the bristles of the brush to the test sample application area in step (g) is acceptable.

Another preferred embodiment of the invention provides a method of testing the capacity of a brush for transferring an acceptable amount of a product (e.g., a cosmetic product) from its bristles to an application surface (e.g., a person's skin).

This method comprises:

(a) providing a test sample application area;

(b) providing a brush comprising bristles having a product deposited thereon;

(c) providing a device for holding the brush at a predetermined position with respect to the test sample application area, the predetermined position being selected so that the bristles of the brush having product deposited thereon may be moved in relative contact with the test sample application area;

(d) placing the brush in the device and moving the bristles of the brush in relative contact with the test sample application area a predetermined distance a predetermined number of times; and (e) determining whether or not the amount of product transferred from the bristles of the brush to the test sample application area in step (d) is acceptable.

A preferred method for carrying out step (e) above comprises utilizing white paper as the material that the brush contacts in step (d) and comparing the color of the white paper after step (d) with the color of a standard.

Product may be deposited on the bristles in step (b) above by a variety of suitable techniques. One suitable technique comprises the steps of:

(f) placing a brush having bristles in the device;

(g) providing a sample of product at a fixed position at the test sample application area; and (h) moving the bristles of the brush in relative contact with the sample of the product a predetermined distance a predetermined number of times to deposit product on the bristles.

The present invention is also directed to an apparatus for producing the various embodiments of the method of the invention. The apparatus of the present invention comprises:

(a) a test sample application area;

(b) a device for holding a brush at a predetermined position with respect to the application area; and (c) means for moving the device with respect to the test sample application area in such a manner that the bristles a brush held in the device may be moved in relative contact with the test sample application area a predetermined distance a predetermined number of times.

Depending on the specific method for which the apparatus is to be used, the test sample application area of the apparatus preferably comprises either (a) a supply of product, or (b) white paper.

The relative movement between the brush bristles and the test sample application area may be made by holding one of either the brush or the test sample application area fixed and moving the other, or by simultaneous motion of both. Movement of the brush may be obtained by, for example, holding the brush in a fixed orientation relative to the test sample application area, or moving the brush, e.g., pivoting the brush about a fixed point or pivoting the brush about a moving point. Optionally, the relative contact may be such that a predetermined pressure of contact is maintained between the brush and the test sample application area.

DETAILED DESCRIPTION OF PREFERRED EMBODIMENTS

Figure 1:
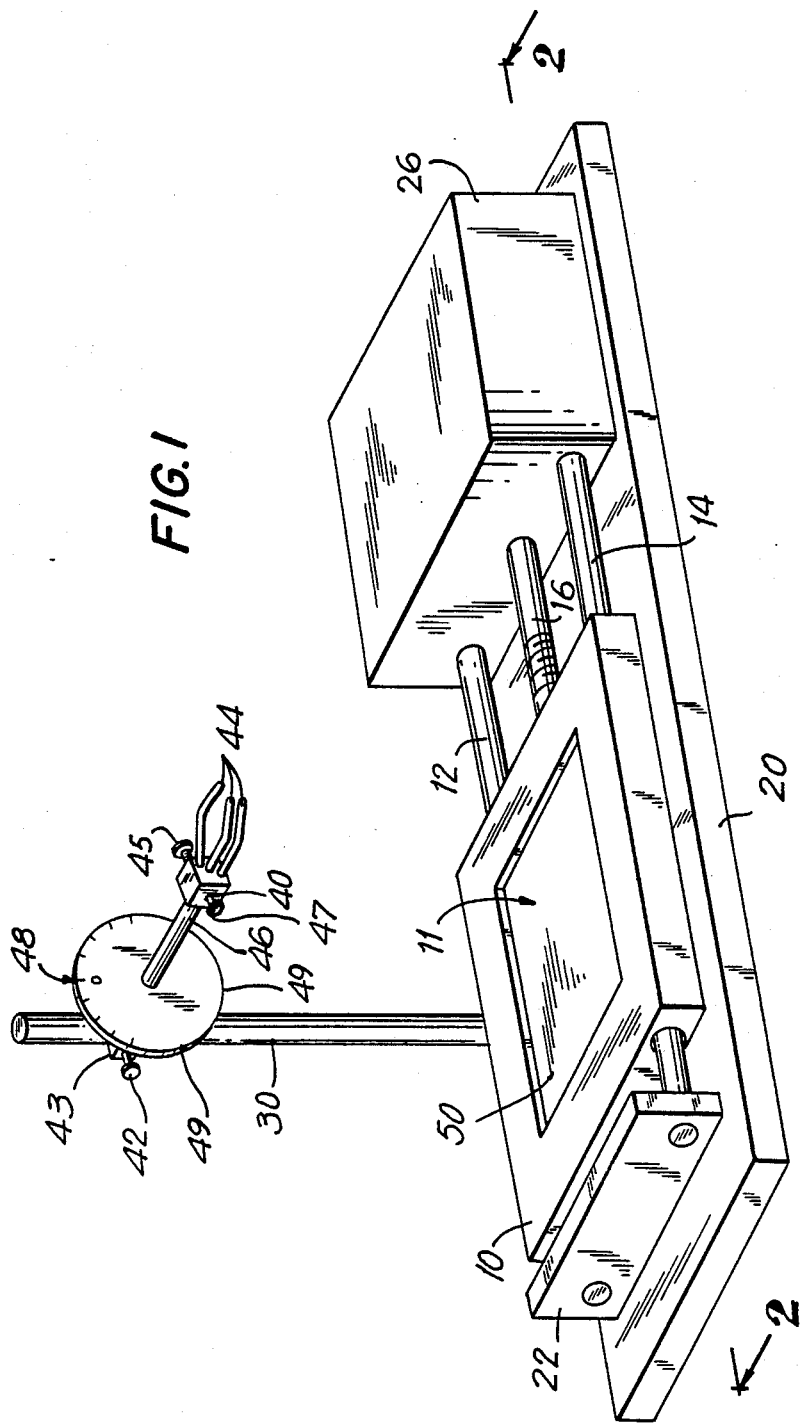
FIG. 1 is a perspective view of a brush tester apparatus in accordance with the present invention.

An apparatus for testing brushes is shown in FIG. 1. Movable platform 10 is mounted on base 20 for reciprocation along guide rails 12 and 14, which are mounted to base 20 between endpiece 22 and housing 26. Housing 26 contains the drive means (not shown in FIG. 1) for reciprocating platform 10 as described herein. Stand 30 is connected to base 20 and rises above platform 10 substantially perpendicular to the plane of the top of platform 10.

Figure 3:
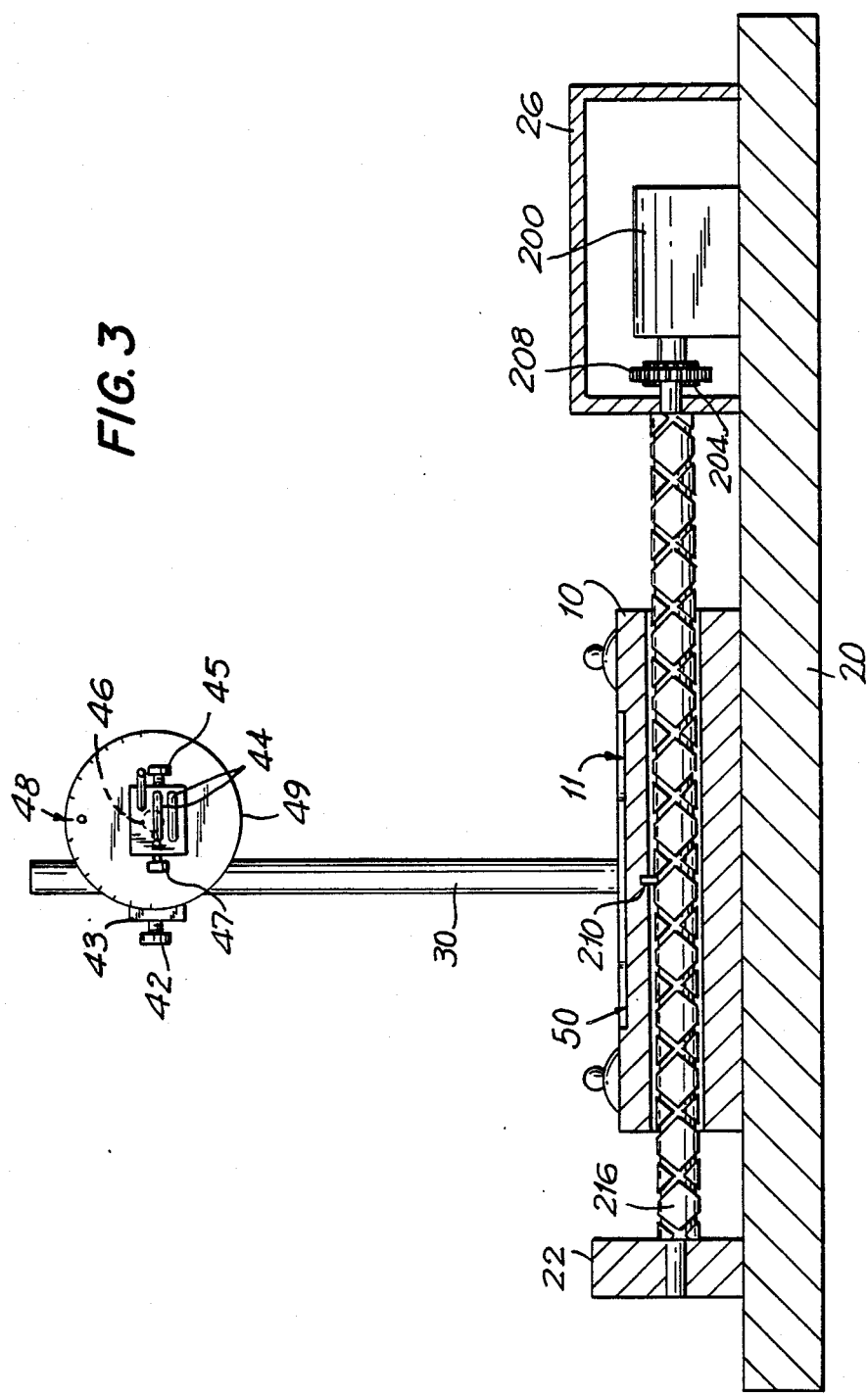
FIG. 3 is a front sectional view of an embodiment of the present invention.

Referring to FIGS. 1 and 3, clamp 40 is mounted on stand 30 so that it may be moved along stand 30 and fixed in location at any height above the platform. Clamp 40 includes fingers 44 for grasping and securely holding a brush, and screw 45 for adjusting the spacing between the fingers to insert, hold, and remove a brush. Clamp 40 extends over platform 10 and is secured at one end of post 46. The other end of post 46 is secured to member 43 by screw 47. Member 43 is secured to stand 30 by screw 42.

In the preferred embodiment, stand 30 and clamp means 40 preferably are adapted for holding the brush at any angle and height relative to platform 10 so that the brush can be positioned to provide a desired angle of attack, that is, the angle formed between the shaft of the brush and the plane of the sample application area, and thereby exert a desired pressure on the bristles as the brush and platform are moved relative to each other. Typically, the pressure is sufficient to cause the bristles to bend and be in contact with the test sample application area, whether paper or product, in the manner that the brush is intended to be used. The angular orientation of post 46, and hence, clamp 40, can be adjusted 360° degrees about the longitudinal axis of post 46 by loosening screw 47 and rotating post 46 to the desired orientation. Although not shown, means for adjusting the angle of post 46 relative to stand 30 may be provided.

Further, the stand and clamp means is preferably provided with marks so that a selected brush height and angle can be recorded and a given test on an identical brush can be repeated under substantially the same test conditions. In the preferred embodiment, secured about post 46 is dial 49 that rotates with post 46 and has marks about its periphery indicating 360° of a compass. Attached to stand 30 is pointer 48 which cooperates with the numbers marked on dial 49 to indicate on dial 49 the particular angular orientation of the clamp.

Figure 2:
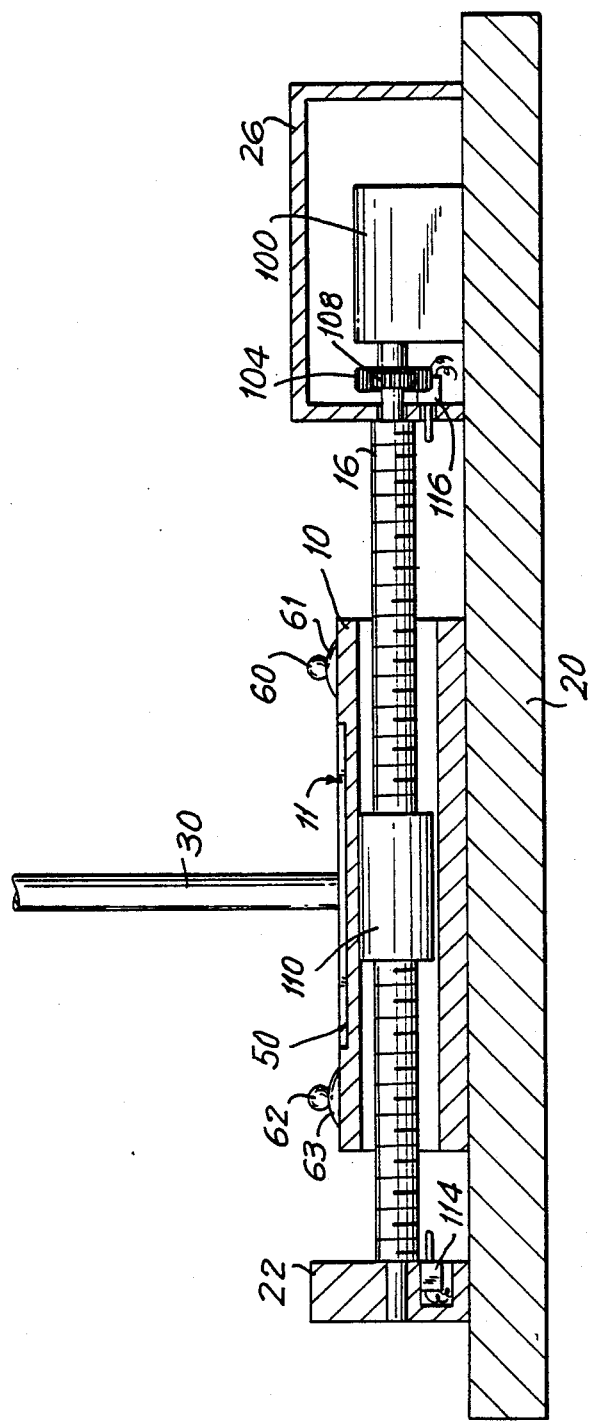
FIG. 2 is front section view of the apparatus of FIG. 1 taken along the lines 2—2.

Referring to FIGS. 1-3, platform 10 includes recess 11 which is adapted to receive a pressed pan of product or a block of material (neither of which are shown). The recess in platform 10 may aid in keeping the pan of product in place and also provide the surface of the product supply being at the same relative height as the paper in the dye or product transfer configuration. Further, the block (not shown) is intended to fit in the recess and provide a support surface for the dye/product transfer test sample application area so that the apparatus can be quickly converted from the dye/product transfer configuration to the product pick-up configuration, e.g., by removing the paper and block and replacing them with a supply of product.

Referring to FIGS. 1-3, means for temporarily securing test sample application area 50 are shown as posts 60 and 62 and corresponding spring clamps 61 and 63. The tension of spring clamps 61 and 63 is sufficient to hold down a sheet of paper or a pan of product, but will permit easy removal. Spring clamps 61 and 63 may be metal or plastic.

Referring to FIG. 2, one embodiment of the means for driving platform 10 is shown. Motor 100 drives gears 104 and 108 which rotates screw 16. Boss 110 has a bore passing therethrough which contains threads that interfit with the threads of screw 16. As screw 16 is rotated, boss 110 will be advanced along the length of screw 16. Limit switches 114 and 116 are located at either end of the desired range of travel of platform 10 so that when boss 110 contacts either limit switch, motor 100 is caused to reverse its direction, and thus, the direction of travel of platform 10.

A circuit means (not shown) may be provided to control the relative motion of the test brush and platform so that the platform will stop, e.g., automatically after a present number of strokes, e.g., 10, have occurred. Using the same brush orientation and the number of strokes permits comparing the results of separate tests.

Referring to FIG. 3, another embodiment of the platform driving means is shown. Motor 200 drives gears 204 and 208 which unidirectionally rotates post 216. Post 216 has two helical grooves that drive pin 210 connected to platform 10 so that one groove causes pin 210 to travel in one direction down the length of post 216 and, at the end of the range of travel, the pin passes into the other groove to travel back along post 216 in the other direction. The ends of the grooves are connected so that the platform oscillates back and forth as long as post 216 is rotating.

It is to be understood that, although the embodiments described herein refer to translational movement of the platform and brush relative to each other, the term stroke also is meant also to include any repeatable pattern of relative motion between the brush bristles and the test sample application area including translational, rotational or a combination thereof. Additional guide means may be provided, e.g., a grooved cam or multiple guide rails at various angles may be provided to obtain he desired stroke patterns.

The method of testing brushes comprises placing a test sample in the platform, placing and securing the brush in the clamp and holder device, adjusting the orientation and height of the brush relative to the test sample to provide a selected height and selected angle of attack and to provide the desired pressure between the bristles and the test sample, and moving the test sample and brush relative to each other for a predetermined number strokes. Thus, a brush may be tested for product pick-up and then tested for transfer to paper of product, if an undyed brush is used, or product and dye if a dyed brush is used, by replacing the product with the block and paper and passing the product loaded brush over the paper.

One method of measuring color is by visual evaluation by a specialist trained in evaluating the pay-off or lay-down of colored products. Although this visual examination technique is subjective, it has long been used in the cosmetic and color transfer fields. Alternately, equipment capable of measuring the color applied to the test sample application area may be employed. Such devices may measure the wavelength of light reflected and compare it to preestablished limits of acceptable colors. Known devices of this type include Macbeth Color Computer available from Macbeth Div. of Kollmorgan Corp. Newburgh, N.Y. Using such apparatus permits establishing a specific accept/reject range or value, for either the purposes of quality control or for determining whether or not a brush under development exhibits satisfactory characteristics.

I claim:
1. A method of testing the capacity of a brush having bristles to pick-up an acceptable amount of product comprising:
    (a) providing a sample of product at a fixed position at a test sample application area;
    (b) providing a device for holding the brush at a predetermined position with respect to the sample of product, the predetermined position being selected so that the bristles of the brush may be moved in relative contact with the sample of product;
    (c) placing the brush in the device and moving the bristles of the brush in relative contact with the sample of product a predetermined distance a predetermined number of times; and
    (d) determining whether or not the amount of product picked-up by the brush in step (c) above is acceptable.

2. The method of claim 1 wherein the amount of product picked-up in step (c) is determined by weighing the brush both before and after step (c) is conducted.

3. The method of claim 1 wherein the amount of product picked-up in step (c) is determined by weighing the sample of product before and after step (c) is conducted.

4. The method of claim 1 further comprising:
    (e) removing the sample of product from the test sample application area;
    (f) after conducting step (d), placing the brush in the device a second predetermined distance from the test sample application area, the second predetermined position being selected so that the bristles of the brush may be moved in relative contact with the test sample application area;

(g) moving the bristles of the brush in relative contact with the test sample application area a predetermined distance a predetermined number of times; and (h) determining whether or not the amount of product transferred from the bristles of the brush to the test sample application area in step (g) is acceptable.

5. The method of claim 4 wherein the test sample application area comprises white paper and the determination in step (h) is made by comparing the color of the white paper after step (g) with the color of a standard.

6. A method of testing the capacity of a brush having bristles for transfering an acceptable amount of a product comprising:

(a) providing a test sample application area;

(b) providing a brush comprising bristles having a product deposited thereon;

(c) providing a device for holding the brush at a predetermined position with respect to the test sample application area, the predetermined position being selected so that the bristles of the brush having product deposited thereon may be moved in relative contact with the test sample application area;

(d) placing the brush in the device and moving the bristles of the brush in relative contact with the test sample application area a predetermined distance a predetermined number of times; and (e) determining whether or not the amount of product transferred from the bristles of the brush to the test sample application area in step (d) is acceptable.

7. The method of claim 6 wherein the test sample application area comprises white paper and the determination in step (e) is made by comparing the color of the white paper after step (d) with the color of a standard.

8. The method of claim 6 wherein product is deposited on the bristles of the brush provided in step (b) by a method comprising:

(f) placing a brush having bristles in the device;

(g) providing a sample of product at a fixed position at the test sample application area;

(h) moving the bristles of the brush in relative contact with the sample of the product a predetermined distance a predetermined number of times to deposit product on the bristles.

* * * * *